(12) United States Patent
Friedlander et al.

(10) Patent No.: US 8,731,807 B2
(45) Date of Patent: *May 20, 2014

(54) EVALUATING ROAD CONDITIONS USING A MOBILE VEHICLE

(71) Applicant: International Business Machines Corporation, Armonk, NY (US)

(72) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/962,665

(22) Filed: Aug. 8, 2013

(65) Prior Publication Data

US 2013/0325308 A1  Dec. 5, 2013

Related U.S. Application Data

(63) Continuation of application No. 13/192,887, filed on Jul. 28, 2011, now Pat. No. 8,538,667.

(51) Int. Cl.
*G06G 7/76* (2006.01)

(52) U.S. Cl.
USPC ........................................................ 701/117

(58) Field of Classification Search
USPC .......................................... 701/117–119, 400
See application file for complete search history.

(56) References Cited

U.S. PATENT DOCUMENTS

| 3,820,381 A | 6/1974 | Thurston |
| 3,838,421 A | 9/1974 | Dasse-Hartaut et al. |
| 4,073,183 A | 2/1978 | Byalko et al. |

(Continued)

FOREIGN PATENT DOCUMENTS

| JP | 52104960 A | 9/1977 |
| JP | 4235380 A | 8/1992 |

(Continued)

OTHER PUBLICATIONS

N. Harrington, "Knock-Based Commands for Your Linux Laptop", pp. 1-11, Jul. 25, 2006, http://www.ibm.com/developerworks/library/I-knockage/index.html.

(Continued)

*Primary Examiner* — Yonel Beaulieu
(74) *Attorney, Agent, or Firm* — John R. Pivnichny; Law Office of Jim Boice (57) ABSTRACT

A method, system, and/or computer program product evaluates a real-time condition of a construct of a roadway. A processor receives a set of roadway acoustic sound patterns from a mobile microphone that is mounted on a terrestrial vehicle as it travels along a roadway. This set of roadway acoustic sound patterns is created by a physical contact between a roadway surface of the roadway and a tire on the terrestrial vehicle. The processor also receives a set of transient data from a probe on the terrestrial vehicle. This transient data describes a real-time transient environmental condition at the roadway. The set of roadway acoustic sound patterns and the set of transient data are input into an analysis algorithm to determine a real-time physical condition of a construct of the roadway. Data describing the real-time physical condition of the construct of the roadway is then transmitted to a remote computer.

20 Claims, 6 Drawing Sheets

(56) References Cited

U.S. PATENT DOCUMENTS

| | | | |
|---|---|---|---|
| 4,186,590 | A | 2/1980 | Egorov et al. |
| 4,511,247 | A | 4/1985 | McGovern et al. |
| 4,530,233 | A | 7/1985 | Kadi |
| 5,195,046 | A | 3/1993 | Gerardi et al. |
| 5,549,803 | A | 8/1996 | Schoess et al. |
| 5,681,986 | A | 10/1997 | Merk et al. |
| 5,736,940 | A | 4/1998 | Burgener |
| 6,260,004 | B1 | 7/2001 | Hays et al. |
| 6,265,979 | B1 | 7/2001 | Chen et al. |
| 6,718,270 | B2 | 4/2004 | Horiuchi et al. |
| 6,950,767 | B2 | 9/2005 | Yamashita et al. |
| 7,228,740 | B2 | 6/2007 | Sinha |
| 7,325,759 | B2 | 2/2008 | Meyer |
| 7,343,136 | B2 | 3/2008 | Liu et al. |
| 7,535,355 | B2 | 5/2009 | Barone |
| 7,627,441 | B2 | 12/2009 | Longsdorf et al. |
| 7,630,948 | B2 | 12/2009 | Friedlander et al. |
| 7,693,663 | B2 | 4/2010 | Friedlander et al. |
| 7,720,574 | B1 | 5/2010 | Roys |
| 7,762,142 | B2 | 7/2010 | Rakow et al. |
| 8,154,723 | B2 | 4/2012 | Fu et al. |
| 8,538,667 | B2 * | 9/2013 | Friedlander et al. .......... 701/117 |
| 2004/0122787 | A1 | 6/2004 | Avinash et al. |
| 2005/0011278 | A1 | 1/2005 | Brown et al. |
| 2005/0256885 | A1 | 11/2005 | Yairi et al. |
| 2006/0071786 | A1 | 4/2006 | Fano |
| 2006/0097983 | A1 | 5/2006 | Haggman et al. |
| 2006/0285350 | A1 | 12/2006 | Wang |
| 2007/0050121 | A1 | 3/2007 | Ammon et al. |
| 2007/0199382 | A1 | 8/2007 | Sakai |
| 2008/0009099 | A1 | 1/2008 | Kishkovich et al. |
| 2008/0077463 | A1 | 3/2008 | Friedlander et al. |
| 2008/0180281 | A1 | 7/2008 | Bilimoria et al. |
| 2008/0270034 | A1 | 10/2008 | Friedlander et al. |
| 2008/0274553 | A1 | 11/2008 | Bratton et al. |
| 2009/0157302 | A1 | 6/2009 | Tashev et al. |
| 2009/0271100 | A1 | 10/2009 | Kim et al. |
| 2010/0150359 | A1 | 6/2010 | Knickrehm et al. |
| 2010/0189291 | A1 | 7/2010 | Aharoni et al. |
| 2010/0268469 | A1 | 10/2010 | Harrison et al. |
| 2011/0085156 | A1 | 4/2011 | Jones et al. |
| 2011/0153208 | A1 | 6/2011 | Kruglick |
| 2011/0173067 | A1 | 7/2011 | Herbst et al. |
| 2011/0308638 | A1 | 12/2011 | Hyland et al. |
| 2013/0030613 | A1 | 1/2013 | Friedlander et al. |
| 2013/0030680 | A1 | 1/2013 | Friedlander et al. |
| 2013/0030724 | A1 | 1/2013 | Friedlander et al. |
| 2013/0030725 | A1 | 1/2013 | Friedlander et al. |
| 2013/0040399 | A1 | 2/2013 | Belbruno et al. |
| 2013/0085671 | A1 | 4/2013 | Friedlander et al. |

FOREIGN PATENT DOCUMENTS

| | | | |
|---|---|---|---|
| JP | 05052972 | U | 7/1993 |
| JP | 07044117 | A | 2/1995 |
| JP | 08085496 | A | 4/1996 |
| JP | 2006194795 | A | 7/2006 |
| JP | 2007531868 | A | 11/2007 |
| WO | 2008052786 | A1 | 5/2008 |
| WO | 2010071607 | A1 | 6/2010 |

OTHER PUBLICATIONS

W. Xie et al., "A New Diagnostic Method of Bolt Loosening Detection for Thermal Protection Systems", Proceedings of the SPIE—The International Society for Optical Engineering, vol. 7493, 2009.

S. Lihua et al., "Applications of Piezoelectric Material Sensors in Smart Structures", Transactions of Nanjing University of Aeronautics & Astronautics, vol. 1, No. 2, 210-213, Dec. 1996.

J. Schoess et al., "Smart Aircraft Fastener Evaluation (SAFE) System—A Condition-Based Corrosion Detection System for Aging Aircraft", Proceedings of the SPIE—The International Society for Optical Engineering, vol. 2718, 175-184, 1996.

J. Schoess et al., "Smart Fastener for KC-135 Structural Integrity Monitoring", Proceedings of the SPIE—The International Society for Optical Engineering, vol. 3042, pp. 278-282, 1997.

T. Bojko, "Smart Sensor Solutions for Mechanical Measurements and Diagnostics", Metrology and Measurement Systems, vol. 12, No. 1, 2005, pp. 95-103.

S. Kessler, "Piezoelectric-Based In-Situ Damage Detection of Composite Materials for Structural Health Monitoring Systems", Doctorate of Philosophy in Aeronautics and Astronautics at the Massachusetts Institute of Technology, 2002, pp. 1-200.

D. Sinha, "Acoustic Sensor for Pipeline Monitoring: Technology Report", Los Alamos National Laboratory, Jul. 20, 2005, pp. 1-23.

B. Umeadi et al., "The Development of an Intelligent Sensor for the Monitoring of Pipeline System Integrity", Oil and Gas 2008, pp. 1-4.

C. Zang et al., "Structural Health Monitoring and Damage Assessment Using Frequency Response Correlation Criteria", Journal of Engineering Mechanics, Sep. 2007, 981-993.

S.L. Hung et al., "Aiming for the Top University Plan: Preliminary Results" 2009, http://www.cv.nctu.edu.tw/~wwwadm/chinese/monitoring2/result.html.

U.S. Appl. No. 11/741,186, Friedlander et al.—Non-Final Office Action Mailed Nov. 21, 2008.

U.S. Appl. No. 11/741,186, Friedlander et al.—Final Office Action Mailed Apr. 15, 2009.

U.S. Appl. No. 11/741,186, Friedlander et al.—Non-Final Office Action Mailed Jul. 9, 2009.

U.S. Appl. No. 11/741,186, Friedlander et al.—Notice of Allowance Mailed Nov. 20, 2009.

R. Marinelli, "FAA Runway Friction Program", Runway Condition Determination, Reporting, and Report Dissemination Workshop, Jun. 20, 2006, pp. 1-13.

T. Yager, "Runway Friction Measurement", FAA/Aviation Industry Workshop on Runway Condition Determination, Reporting, and Report Dissemination, Aug. 7-8, 2006, pp. 1-15.

Douglas Equipment International Inc., Special Products Division "MU-Meter MK 6—Specification" PDF Retrieved From http://www.douglas-equipment.com/product_display.php?id=0000000035, pp. 1-2.

U.S. Appl. No. 13/192,887—Non-Final Office Action Mailed Feb. 7, 2013.

United Kingdom Patent Application No. GB1216790.4, Combined Search and Examination Report, Jan. 18, 2013, pp. 1-5.

International Searching Authority, International Search Report and Written Opinion for PCT/IB2012/053753, Dec. 18, 2012, pp. 1-6.

U.S. Appl. No. 13/252,342—Non-Final Office Action Mailed Nov. 9, 2012.

U.S. Appl. No. 13/190,172—Non-Final Office Action Mailed Sep. 25, 2013.

U.S. Appl. No. 13/192,149—Non-Final Office Action Mailed Sep. 27, 2013.

U.S. Appl. No. 13/192,149—Final Office Action Mailed Feb. 26, 2014.

* cited by examiner

EVALUATING ROAD CONDITIONS USING A MOBILE VEHICLE

The present application is a continuation of U.S. patent application Ser. No. 13/192,887, now issued as U.S. Pat. No. 8,538,667 B2), filed on Jul. 28, 2011 and issued on Sep. 17, 2013, and entitled, "Evaluating Road Conditions Using a Mobile Vehicle," which is incorporated herein by reference in its entirety.

BACKGROUND

The present disclosure relates to the field of electronics, and specifically to electronic devices used to measure vibration. Still more particularly, the present disclosure relates to electronic sensors used to evaluate the physical condition of a roadway.

Vibration detection devices are used to detect and transpose mechanical vibration energy into analogous electrical signals that represent the detected mechanical vibration energy. A vibration detection device uses a motion sensitive component, such as an accelerometer, a piezoelectric device (e.g., a tuned crystal), etc. to make these mechanical-to-electrical transformations.

SUMMARY

A method, system, and/or computer program product evaluates a real-time condition of a construct of a roadway. A processor receives a set of roadway acoustic sound patterns from a mobile microphone that is mounted on a terrestrial vehicle as it travels along a roadway. This set of roadway acoustic sound patterns is created by a physical contact between a roadway surface of the roadway and a tire on the terrestrial vehicle. The processor also receives a set of transient data from a probe on the terrestrial vehicle. This transient data describes a real-time transient environmental condition at the roadway. The set of roadway acoustic sound patterns and the set of transient data are input into an analysis algorithm to determine a real-time physical condition of a construct of the roadway. Data describing the real-time physical condition of the construct of the roadway is then transmitted to a remote computer.

DETAILED DESCRIPTION

As will be appreciated by one skilled in the art, the present invention may be embodied as a system, method, or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java (JAVA is a registered trademark of Sun Microsystems, Inc. in the United States and other countries), Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Figure 1:
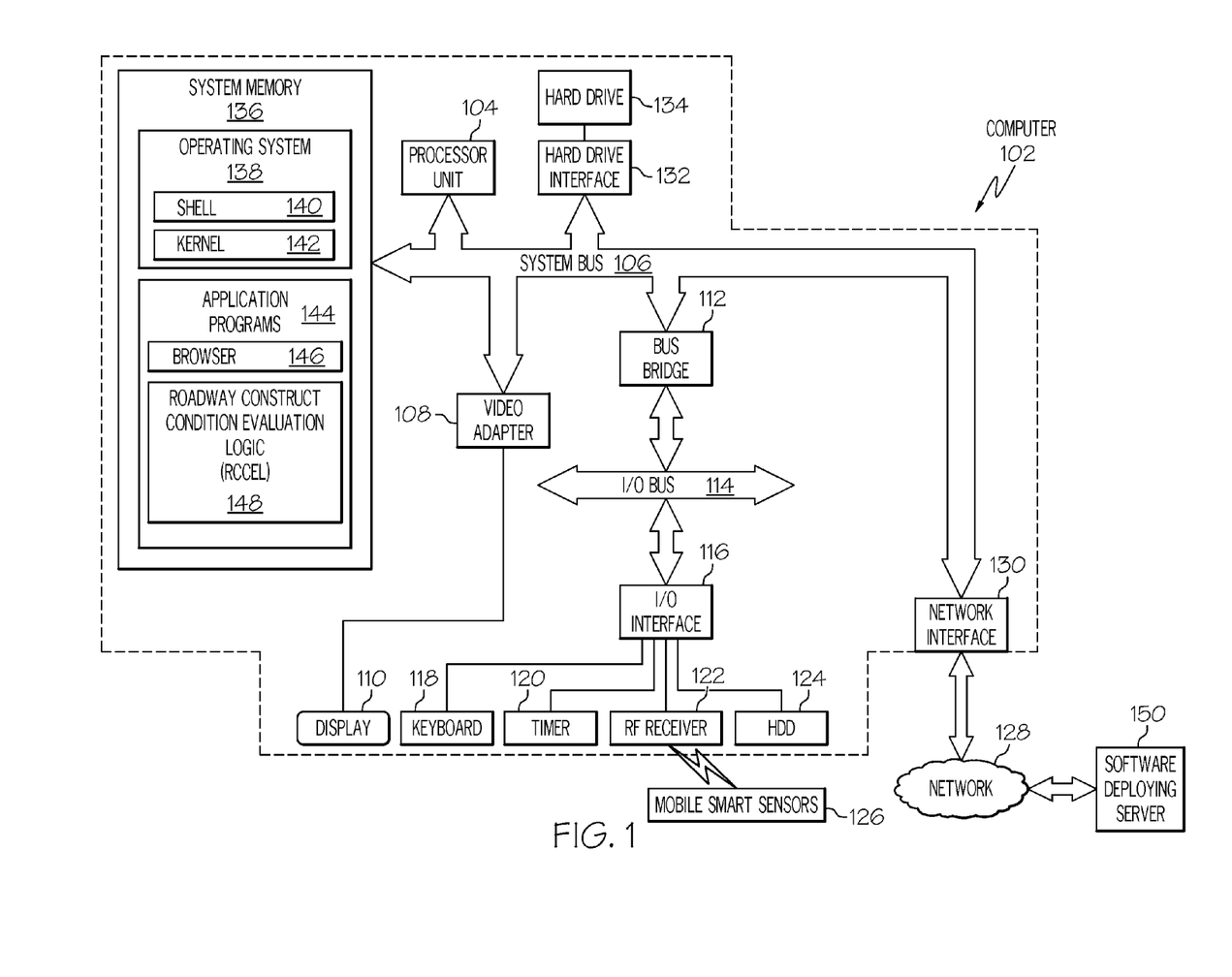
FIG. 1 depicts an exemplary computer that may be utilized by the present invention.

With reference now to the figures, and in particular to FIG. 1, there is depicted a block diagram of an exemplary computer 102, which the present invention may utilize. Note that some or all of the exemplary architecture shown for computer 102 may be utilized by software deploying server 150.

Computer 102 includes a processor unit 104, which may utilize one or more processors each having one or more processor cores, that is coupled to a system bus 106. A video adapter 108, which drives/supports a display 110, is also coupled to system bus 106. System bus 106 is coupled via a bus bridge 112 to an Input/Output (I/O) bus 114. An I/O interface 116 is coupled to I/O bus 114. I/O interface 116 affords communication with various I/O devices, including a keyboard 118, a timer 120, a Radio Frequency (RF) receiver 122, a Hard Disk Drive (HDD) 124, and mobile smart sensors 126, which communicate wirelessly with the RF receiver 122. Examples of mobile smart sensors 126 include, but are not limited to, mobile smart sensor(s) 226 shown below in FIG. 2, as well as mobile smart sensor 326 depicted in FIG. 3. Note that the format of the ports connected to I/O interface 116 may be any known to those skilled in the art of computer architecture, including but not limited to Universal Serial Bus (USB) ports.

Computer 102 is able to communicate with a software deploying server 150 via a network 128 using a network interface 130, which is coupled to system bus 106. Network 128 may be an external network such as the Internet, or an internal network such as an Ethernet or a Virtual Private Network (VPN).

A hard drive interface 132 is also coupled to system bus 106. Hard drive interface 132 interfaces with a hard drive 134. In a preferred embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a World Wide Web (WWW) client (i.e., computer 102) to send and receive network messages to the Internet using HyperText Transfer Protocol (HTTP) messaging, thus enabling communication with software deploying server 150 and other described computer systems.

Application programs 144 in computer 102's system memory (as well as software deploying server 150's system memory) also include a Roadway Construct Condition Evaluation Logic (RCCEL) 148. RCCEL 148 includes code for implementing the processes described below, and particularly as described in reference to FIGS. 2-6. In one embodiment, computer 102 is able to download RCCEL 148 from software deploying server 150, including in an on-demand basis. Note further that, in one embodiment of the present invention, software deploying server 150 performs all of the functions associated with the present invention (including execution of RCCEL 148), thus freeing computer 102 from having to use its own internal computing resources to execute RCCEL 148.

The hardware elements depicted in computer 102 are not intended to be exhaustive, but rather are representative to highlight essential components required by the present invention. For instance, computer 102 may include alternate memory storage devices such as magnetic cassettes, Digital Versatile Disks (DVDs), Bernoulli cartridges, and the like. These and other variations are intended to be within the spirit and scope of the present invention.

Note that while the computer 102 may be on a mobile vehicle (i.e., the terrestrial vehicle 202 shown in FIG. 2 below), computer 102 may alternatively be in another location (fixed or mobile) that is remote from the mobile vehicle. That is, the computer 102 may be "on-board" the mobile vehicle, may be at a permanent location (e.g., an office building or highway department field location), or it may be on another vehicle which is in remote communication with the first mobile vehicle.

Figure 2:
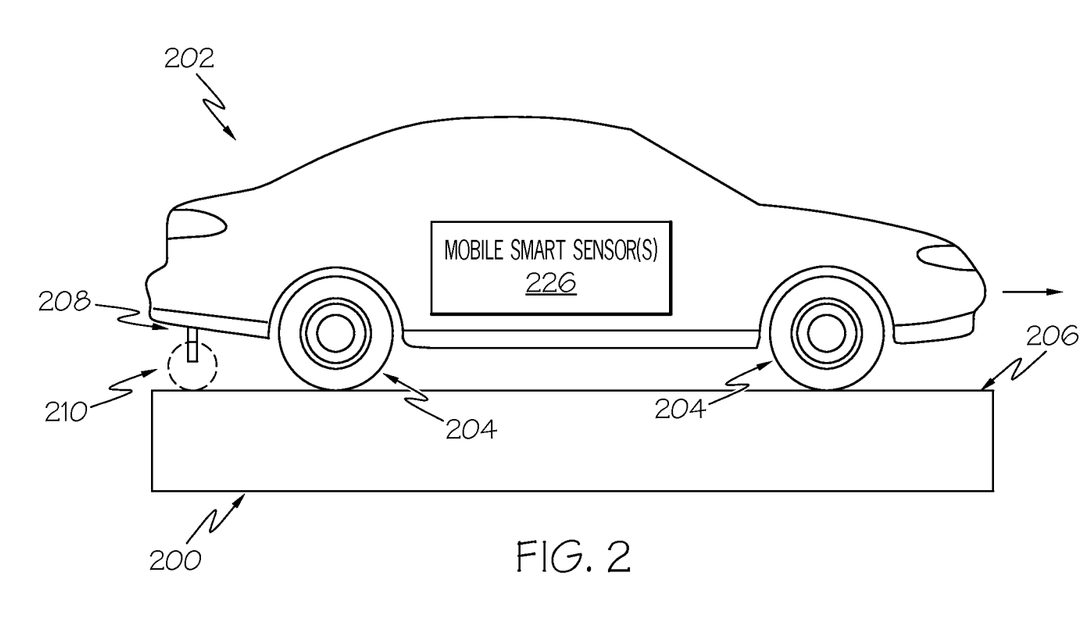
FIG. 2 illustrates an exemplary terrestrial vehicle on which mobile smart sensors are mounted.

With reference now to FIG. 2, an exemplary roadway 200, whose construct is evaluated in real-time in accordance with the present disclosure, is presented. As used herein, the term "construct" is defined as the arrangement of components used in the construction of the roadway 200. That is, the condition of the construct of the roadway describes the physical condition of components used to build the roadway, such as concrete, rebar, asphalt topping, paint, etc., and does not include (specifically excludes) extraneous matter such as windblown dirt, ice, rain water, etc. that may have accumulated on the surface of the roadway after it was constructed.

As depicted in FIG. 2, a terrestrial vehicle 202 (e.g., a self-propelled truck, car, etc., or a towed vehicle such as a trailer) is traveling along the roadway 200. Tires 204 on the terrestrial vehicle 202 make contact with a roadway surface 206 of the roadway 200 as the terrestrial vehicle 202 travels along the roadway 200. This contact results in a distinctive set of roadway vibration patterns, based on the current real-time condition of the construct of the roadway 200, which is detected by the mobile smart sensor(s) 226 (analogous to the mobile smart sensors 126 shown in FIG. 1). The mobile smart sensor(s) 226 includes a sensor that transduces mechanical vibration of the construct of the roadway 200 into an analog vibration pattern, which can then be digitized using a Fast Fourier Transform (FFT) algorithm, which determines a set of underlying frequency components of the mechanical vibration patterns. These frequency components are then digitized for transmission, storage and/or use in rapid future comparison operations.

In one embodiment, a probe 208, used to detect environment conditions on or around the roadway 200, can be affixed to the terrestrial vehicle 202. In one embodiment, probe 208 has a mechanical sensor (not shown), which detects mechanical vibrations that occur as a wheel 210, affixed to the bottom of the probe 208, rolls along the roadway surface 206.

Figure 3:
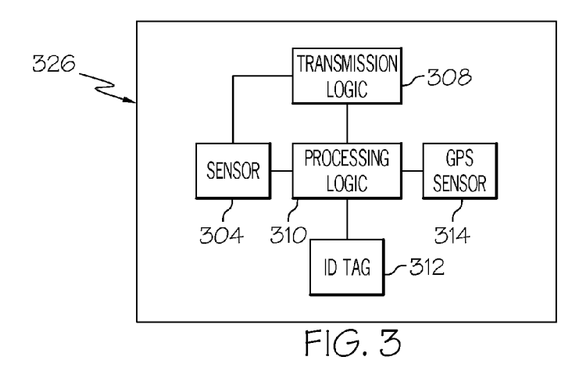
FIG. 3 depicts additional detail of the mobile smart sensor that is mounted on the terrestrial vehicle shown in FIG. 2.

Additional detail of an exemplary mobile smart sensor, such as the mobile smart sensor(s) 226 depicted in FIG. 2 is illustrated in FIG. 3 as a Global Positioning System (GPS) enabled mobile smart sensor 326. Within the GPS-enabled mobile smart sensor 326 is a sensor 304. Sensor 304 is able to sense mechanical vibration (i.e., vibrations that result from the physical interfacing of tires 204 and roadway surface 206 as the terrestrial vehicle 200 in FIG. 2 travels along the roadway 200). In one embodiment, sensor 304 is also able to detect acoustic vibration, such as sound that propagates through air from the physical interfacing of tires 204 (and/or wheel 210) and roadway surface 206 as the terrestrial vehicle 202 in FIG. 2 travels along the roadway 200.

In one embodiment, sensor 304 is directly coupled to a transmission logic 308, which is able to transmit the raw information detected by the sensor 304 to a receiver (e.g., RF receiver 122 shown in FIG. 1). For example, assume that sensor 304 detects mechanical vibrations through the use of an internal crystal-based strain gauge and/or accelerometer. The sensor 304 transduces these mechanical vibrations into electrical analog signals, which are directly transmitted by the transmission logic 308. In another embodiment, however, the transduced mechanical vibrations are first sent to a local processing logic 310 within the GPS-enabled mobile smart sensor 326. This processing logic 310 is able to quantify and digitize the transduced mechanical vibrations before they are sent to the transmission logic 308.

Note that in one embodiment, an identification (ID) tag 312 is also an affixed component of the GPS-enabled mobile smart sensor 326. The affixed ID tag 312 provides a unique identification number for a particular GPS-enabled mobile smart sensor 326. Furthermore, a GPS sensor 314 provides a real-time physical location of the GPS-enabled mobile smart sensor 326, such that any vibration patterns generated by the GPS-enabled mobile smart sensor 326 can be correlated to a specific location on the roadway being monitored.

Figure 4:
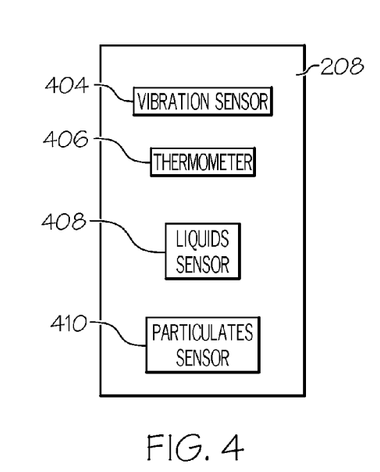
FIG. 4 illustrates additional detail of an environmental probe that is mounted on the terrestrial vehicle shown in FIG. 2.

With reference now to FIG. 4, additional detail of the probe 208 shown in FIG. 2 is presented. Note that in one embodiment, probe 208 includes a vibration sensor 404, which performs the same function as the sensor 304 shown in FIG. 3. However, the mechanical vibrations being detected by vibration sensor 404 are from the wheel 210, not from the tires 204, shown in FIG. 2.

Probe 208 also includes a thermometer 406, a liquids sensor 408, and/or a particulates sensor 410. Thermometer 406 detects a temperature on the roadway surface. A temperature on the roadway surface may be shown to be out-of-range by thermometer 406. An out-of-range temperature is defined as a temperature that is higher than a first pre-determined temperature or lower than a second pre-determined temperature. If the temperature exceeds the upper range limit for the roadway surface, melting or other events may affect the roadway vibration patterns detected by probe 208. Similarly, if the temperature drops below the lower range limit for the roadway surface, ice cracking and other events may affect the roadway vibration patterns detected by probe 208. Liquids sensor 408 detects any liquids (rain, oil, etc.) that are present on the roadway surface. Liquids sensor 408 is also able to detect the current humidity levels at the vehicle 202. Particulates sensor 410 detects any particulates (e.g., dust, dirt, leaves, etc.) that are present on the roadway surface. These conditions/elements (e.g., freezing temperature, rain, dirt, etc.) are real-time transient environmental conditions that an analysis logic such as RCCEL 148 (shown in FIG. 1) will filter out of vibration patterns detected by vibration sensors such as mobile smart sensors 126, sensor 304, and/or vibration sensor 404 described herein. That is, if the roadway surface 206 is clean (free of rain, dirt, etc.) and the temperature is not out-of-range, then a "true" set of roadway vibration patterns are generated by the mobile smart sensors to reflect the true condition of the construct of the roadway. However, if there is water/snow/dirt/etc. on the roadway surface, this will alter the vibration patterns generated by the contact between the vehicle's tires and the roadway surface. Thus, data describing these real-time transient environmental conditions are analytically "removed" from the detected vibration patterns, in order to create the "true" set of roadway vibration patterns.

Figure 5:
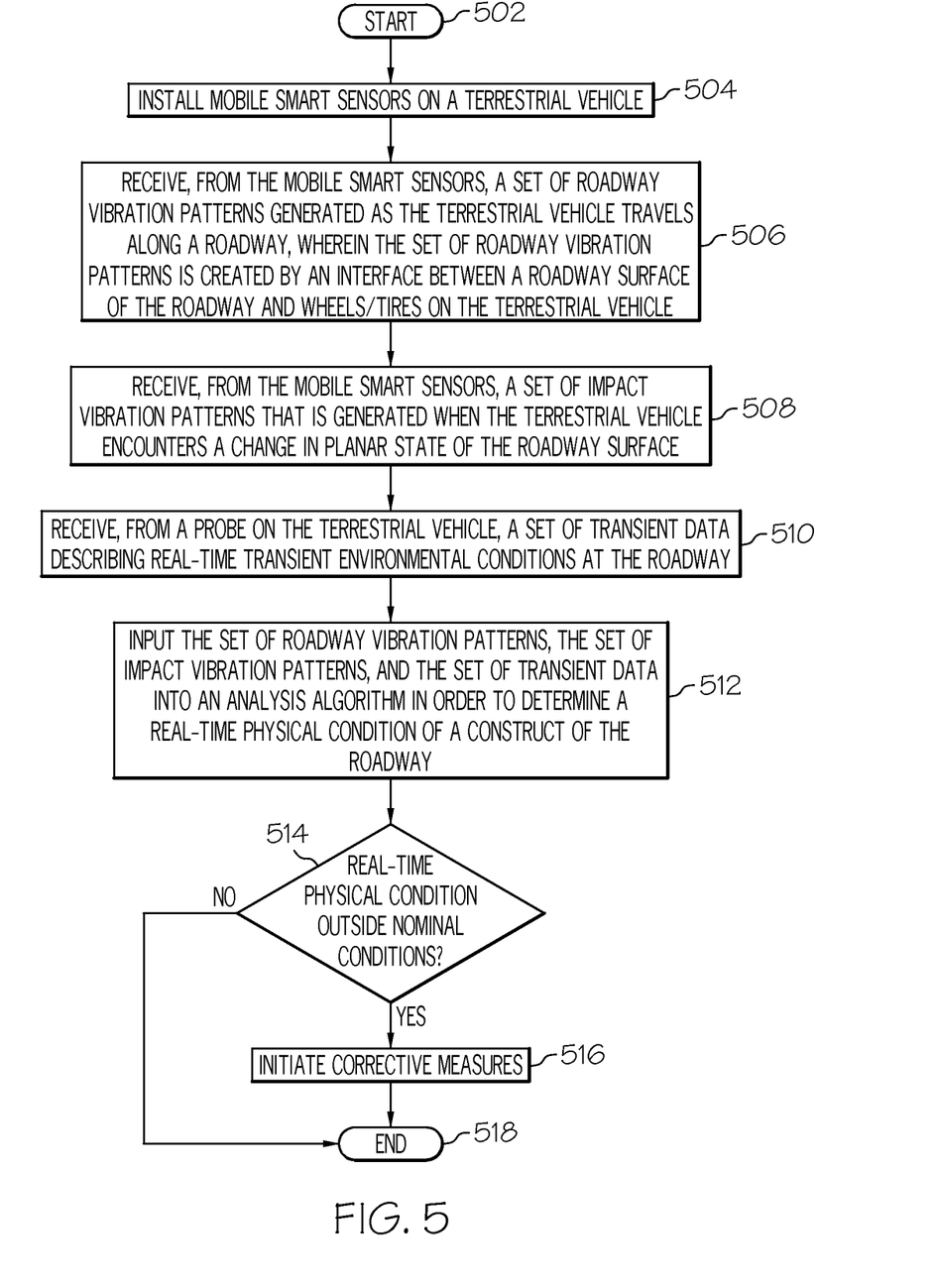
FIG. 5 is a high level flow chart of one or more steps performed by a processor to evaluate a real-time condition of a roadway.

With reference now to FIG. 5, a high level flow chart of one or more steps performed by a processor to evaluate a real-time condition of a roadway is presented. After initiator block 502, a set of mobile smart sensors is installed on a terrestrial vehicle (block 504). These mobile smart sensors are capable of transducing vibration energy from the interface between vehicular tires and a roadway surface. That is, the mobile smart sensors detect and transduce mechanical vibrations that result from the interface between the vehicular tires and the roadway surface to generate a frequency (F) and amplitude (A) vibration pattern, which can be digitized (e.g., through the use of a Fast Fourier Transform (FFT) algorithm) for storage and/or transmission to a remote computer.

As described in block 506, a processor (e.g., processor unit 104 shown in FIG. 1) receives, from the mobile smart sensors, a set of roadway vibration patterns generated as the terrestrial vehicle travels along a roadway. As stated herein, this set of roadway vibration patterns is created by an interface between a roadway surface of the roadway and tires on the terrestrial vehicle. These tires may be the tires that actually support the terrestrial vehicle (e.g., the drive train and/or steering tires 204 shown in FIG. 2), or they may be wheel 210 that is mounted to probe 208.

As described in block 508, the processor can also receive, from the mobile smart sensor, a set of impact vibration patterns that is generated in response to the terrestrial vehicle encountering a change in a planar state of the roadway surface. The "planar state" is defined as the level of elevation consistency of the roadway surface. For example, if the roadway is smooth and level, it has a different planar state than a roadway that is rutted, has potholes, etc. Thus, the mobile smart sensor is able to detect if the tire/wheel has slipped into a run, hit a pothole, etc.

As described in block 510, the processor receives a set of transient data from the probe 208 on the terrestrial vehicle 202. This transient data describes a real-time transient environmental condition at the roadway, such as a presence of liquid (e.g., water, oil, etc.) on a surface of the roadway, a presence of particulates (e.g., dirt, dust, debris, etc.) on the surface of the roadway, a freezing temperature on a surface of the roadway, etc.

As described in block 512, the processor then inputs the set of roadway vibration patterns and the set of transient data into an analysis algorithm (e.g., RCCEL 148 shown in FIG. 1) in order to determine a real-time physical condition of a construct of the roadway. As described herein, the analysis algorithm removes any effect the set of transient data has on the set of roadway vibration patterns. For example, consider the set of roadway vibration patterns 602 shown in FIG. 6. This set of roadway vibration patterns 602 is a temporal frequency and amplitude pattern of vibration readings taken by the mobile smart sensors. The probe 208 described herein has also taken measurements of transient data 604 that describes real-time transient environmental conditions, such as the parts-per-million (PPM) of particulates being kicked up by the tires as they role across the roadway surface, PPMs of liquids being kicked up by the tires, temperature at or near the roadway surface, humidity, etc. being experienced by the terrestrial vehicle at the time the set of roadway vibration patterns 602 are being generated. Thus, the term "transient" is defined as describing conditions that are not part of the original construct of the roadway, but rather are temporary conditions that change as the weather changes, as garbage is blown on the roadway, as dust and dirt accumulates on the roadway, etc.

Figure 6:
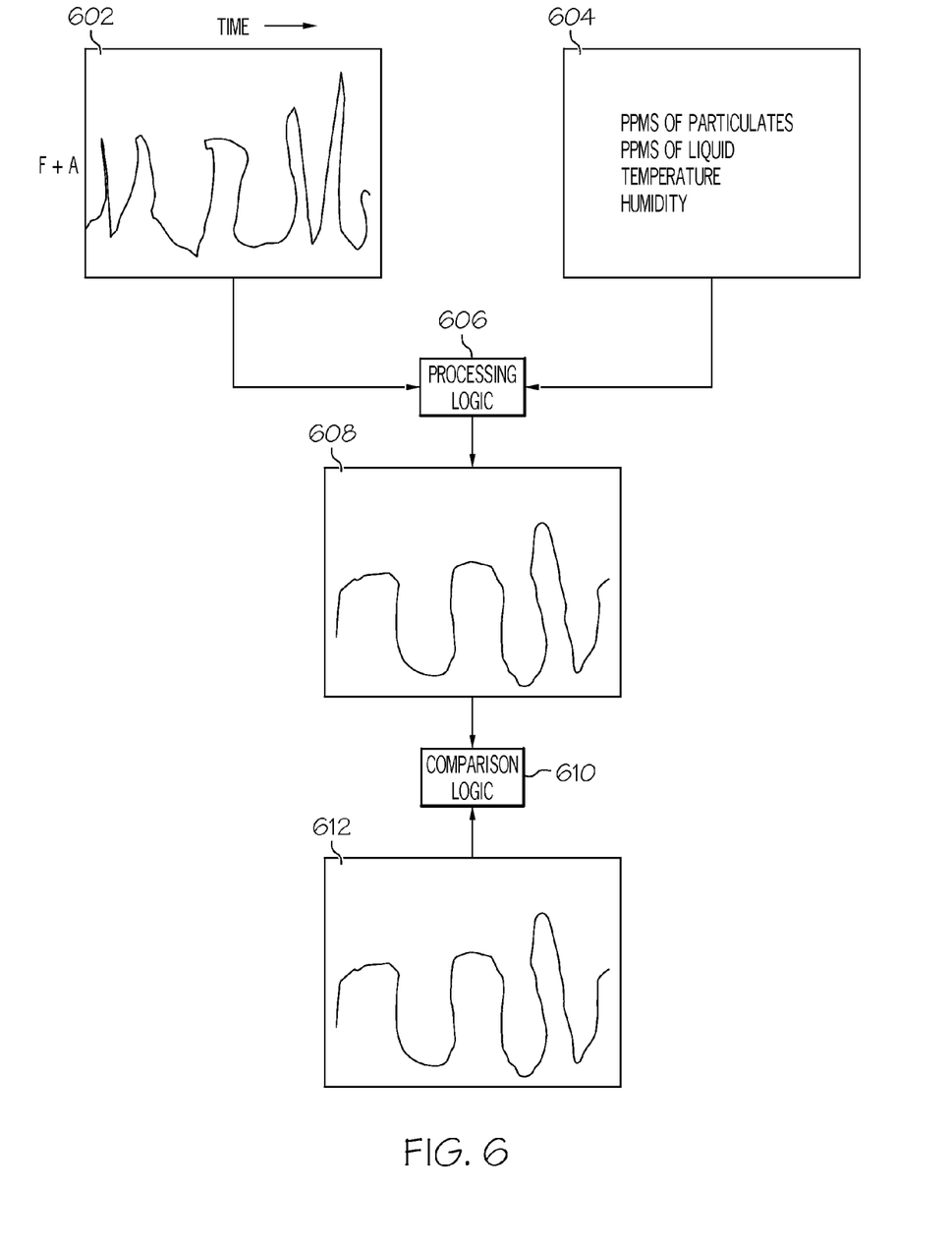
FIG. 6 depicts an exemplary set of frequency (F) plus amplitude (A) roadway vibration patterns and a set of transient data being input into a processing logic to determine a real-time condition of a construct of a roadway.

The processing logic 606 (e.g., RCCEL 148 shown in FIG. 1) takes these real-time transient environmental conditions (i.e., transient data 604) as additional inputs, in order to modify the set of roadway vibration patterns 602 to create the normalized set of roadway vibration patterns 608. The normalized set of roadway vibration patterns 608 depicts the vibration pattern that would have been generated by the interface between the tires and the roadway surface in the absence of any water/snow/dirt/etc. Thus, the normalized set of roadway vibration patterns 608 is a "normalized" (i.e., any transient conditions that may mask the true condition of the construct of the roadway are removed) version of the set of roadway vibration patterns 602. This normalized set of roadway vibration patterns 608 is used by a comparison logic (e.g., RCCEL 148 shown in FIG. 1) in order to locate a stored known set of roadway vibration patterns 612. The known set of roadway vibration patterns 612 was generated on the same stretch of roadway, on another stretch of roadway, or during simulation of the type of roadway that the terrestrial vehicle is traveling across, and describes a known condition of the construct of such a roadway. That is, set of roadway vibration patterns 612 may be the set of vibration patterns generated by the same or a substantially similar terrestrial vehicle as it travels along a similar roadway that has severe rutting. Other vibration patterns (not shown) are those that would be generated as the terrestrial vehicle encounters, on the same or a substantially similar roadway, potholes, crumbing topcoat surfaces, etc. Note again that transient conditions (e.g., rain, snow, etc.) are not identified, but rather are filtered out of the set of vibration patterns generated/collected.

Figure 7:
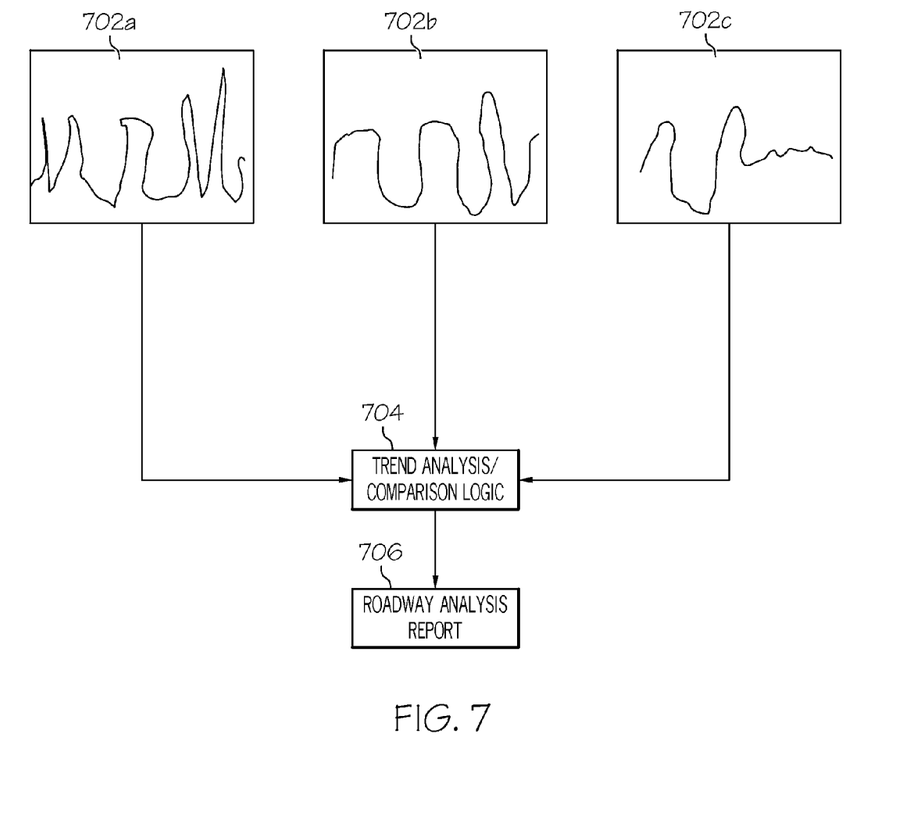
FIG. 7 illustrates a series of sets of roadway vibration patterns used to determine a trend in a condition of the construct of the roadway.

In one embodiment, the analysis algorithm described in block 512 looks for a trend in vibration patterns for a same stretch or road. For example, consider the series of sets of roadway vibration patterns 702a-c shown in FIG. 7. Each of the sets of roadway vibration patterns 702a-c differs from one another, due to a change in the condition of the construct of the roadway over time. The analysis algorithm, shown as trend analysis/comparison logic 704 (e.g., part of RCCEL 148 shown in FIG. 1) is thus able to generate a roadway analysis report 706, which describes this deterioration pattern/rate.

Returning to block 512 in FIG. 5, in one embodiment processor also inputs the set of impact vibration patterns into the analysis algorithm in order to further determine the real-time physical condition of the construct of the roadway. These impact vibration patterns, which detect the change in the planar state of the roadway surface (e.g., potholes, rutting, etc.), further define the real-time physical condition of the construct of the roadway.

By utilizing one or more of the set of roadway vibration patterns, the set of impact vibration patterns, and the set of transient data as inputs to the analysis algorithm, the processor is thus able to generate a report that describes the real-time physical condition of the construct of the roadway.

As depicted in query block 514, if the real-time physical condition of the construct of the roadway falls outside of predetermined nominal range (i.e., if the roadway has become too rutted, has too many potholes, etc.), then corrective measures are initiated (block 516). Such corrective measures may include returning a physical condition of the roadway back within the predetermined nominal range (e.g., by filling in potholes, resurfacing the roadway, replacing sections of the roadway, etc.). In another embodiment, these corrective measures include rerouting traffic away from the roadway, either to reduce the deterioration trend of the roadway, or until the real-time physical conditions of the construct of the roadway return back within the predetermined nominal range (i.e., after construction repairs are completed). This rerouting can be achieved by something as simple as a local rerouting sign, to something as complex as a series of electronic signage that reroutes traffic before it reaches the defective area. The process ends at terminator block 518, which may occur when the mobile terrestrial vehicle is no longer moving.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A method of evaluating a real-time physical condition of a construct of a roadway, the method comprising:

receiving, by a processor executing instructions from a non-transitory computer readable storage media, a set of roadway acoustic sound patterns from a mobile microphone, wherein the mobile microphone is mounted on a terrestrial vehicle that is traveling on a roadway, and wherein the set of roadway acoustic sound patterns describes an oscillation of air pressure that is created by a physical contact between a roadway surface of the roadway and at least one tire on the terrestrial vehicle;

receiving, by the processor executing instructions from the non-transitory computer readable storage media, a set of transient data from a probe on the terrestrial vehicle, wherein the transient data describes a real-time transient environmental condition at the roadway;

inputting, by the processor executing instructions from the non-transitory computer readable storage media, the set of roadway acoustic sound patterns and the set of transient data into an analysis algorithm in order to generate a set of data that describes real-time physical conditions of a construct of the roadway, wherein the analysis algorithm removes any effect the set of transient data has on the set of roadway acoustic sound patterns; and transmitting, by the processor executing instructions from the non-transitory computer readable storage media, the set of data that describes the real-time physical condition of the construct of the roadway to a receiver on a remote computing device.

2. The method of claim 1, further comprising:

determining, by the processor executing instruction from the non-transitory computer readable storage media, the real-time physical conditions of the construct of the roadway by comparing the set of roadway acoustic sound patterns to a known set of roadway acoustic sound patterns.

3. The method of claim 1, further comprising:

determining, by the processor executing instruction from the non-transitory computer readable storage media, that data describing the real-time physical conditions of the construct of the roadway fall outside a predetermined nominal range; and initiating, by the processor executing instruction from the non-transitory computer readable storage media, corrective measures to return a physical condition of the roadway back within the predetermined nominal range.

4. The method of claim 1, further comprising:

determining, by the processor executing instruction from the non-transitory computer readable storage media, that data describing the real-time physical conditions of the construct of the roadway fall outside a predetermined nominal range; and initiating, by the processor executing instruction from the non-transitory computer readable storage media, corrective measures to reroute traffic away from the roadway until the real-time physical conditions of the construct of the roadway return back within the predetermined nominal range.

5. The method of claim 1, further comprising:

analyzing, by the processor executing instruction from the non-transitory computer readable storage media, a series of sets of roadway acoustic sound patterns in order to determine a trend in a deterioration of a physical condition of the construct of the roadway.

6. The method of claim 1, further comprising:

generating, by the processor executing instruction from the non-transitory computer readable storage media, a report that describes the real-time physical condition of the construct of the roadway.

7. The method of claim 1, wherein the real-time transient environmental condition at the roadway is a presence of liquid on a surface of the roadway.

8. The method of claim 1, wherein the real-time transient environmental condition at the roadway is an out-of-range temperature on a surface of the roadway.

9. The method of claim 1, further comprising:

receiving, from the mobile microphone, a set of acoustic sound patterns that is generated in response to the terrestrial vehicle encountering a change in a planar state of the roadway surface; and inputting, by the processor executing instruction from the non-transitory computer readable storage media, the set of acoustic sound patterns, which is generated in response to the terrestrial vehicle encountering the change in the planar state of the roadway surface, into the analysis algorithm in order to further determine the real-time physical condition of the construct of the roadway.

10. A computer program product for evaluating a real-time physical condition of a construct of a roadway, the computer program product comprising:

a non-transitory computer readable storage media;

first program instructions to receive a set of roadway acoustic sound patterns from a mobile microphone, wherein the mobile microphone is mounted on a terrestrial vehicle that is traveling on a roadway, and wherein the set of roadway acoustic sound patterns describes an oscillation of air pressure that is created by a physical contact between a roadway surface of the roadway and at least one tire on the terrestrial vehicle;

second program instructions to receive a set of transient data from a probe on the terrestrial vehicle, wherein the transient data describes a real-time transient environmental condition at the roadway;

third program instructions to receive an input of the set of roadway acoustic sound patterns and the set of transient data into an analysis algorithm in order to generate a set of data that describes real-time physical conditions of a construct of the roadway, wherein the analysis algorithm removes any effect the set of transient data has on the set of roadway acoustic sound patterns;

fourth program instructions to transmit the set of data that describes the real-time physical condition of the construct of the roadway to a receiver on a remote computing device;

and wherein
the first, second, third, and fourth program instructions are stored on the non-transitory computer readable storage media.

11. The computer program product of claim 10, further comprising:

fifth program instructions to determine that data describing the real-time physical conditions of the construct of the roadway fall outside a predetermined nominal range; and sixth program instructions to initiate corrective measures to return a physical condition of the roadway back within the predetermined nominal range; and wherein the fifth and sixth program instructions are stored on the non-transitory computer readable storage media.

12. The computer program product of claim 10, further comprising:

fifth program instructions to determine that data describing the real-time physical conditions of the construct of the roadway fall outside a predetermined nominal range; and sixth program instructions to initiate corrective measures to reroute traffic away from the roadway until the real-time physical conditions of the construct of the roadway return back within the predetermined nominal range; and wherein the fifth and sixth program instructions are stored on the non-transitory computer readable storage media.

13. The computer program product of claim 10, further comprising:
fifth program instructions to generate a report that describes the real-time physical condition of the construct of the roadway; and wherein
the fifth program instructions are stored on the non-transitory computer readable storage media.

14. The computer program product of claim 10, wherein the real-time transient environmental condition at the roadway is particulates on a surface of the roadway.

15. The computer program product of claim 10, wherein the real-time transient environmental condition at the roadway is liquid on a surface of the roadway.

16. The computer program product of claim 10, wherein the real-time transient environmental condition at the roadway is an out-of-range temperature on a surface of the roadway.

17. A system comprising:
a processor, a computer readable memory, and a computer readable storage media;
first program instructions to receive a set of roadway acoustic sound patterns from a mobile microphone, wherein the mobile microphone is mounted on a terrestrial vehicle that is traveling on a roadway, and wherein the set of roadway acoustic sound patterns describes an oscillation of air pressure that is created by a physical contact between a roadway surface of the roadway and at least one tire on the terrestrial vehicle;
second program instructions to receive a set of transient data from a probe on the terrestrial vehicle, wherein the transient data describes a real-time transient environmental condition at the roadway;
third program instructions to receive an input of the set of roadway acoustic sound patterns and the set of transient data into an analysis algorithm in order to generate a set of data that describes real-time physical conditions of a construct of the roadway, wherein the analysis algorithm removes any effect the set of transient data has on the set of roadway acoustic sound patterns;
fourth program instructions to transmit the set of data that describes the real-time physical condition of the construct of the roadway to a receiver on a remote computing device;
and wherein
the first, second, third, and fourth program instructions are stored on the computer readable storage media for execution by the processor via the computer readable memory.

18. The system of claim 17, further comprising:
fifth program instructions to determine the real-time physical conditions of the construct of the roadway by comparing the set of roadway acoustic sound patterns to a known set of roadway acoustic sound patterns; and wherein the fifth program instructions are stored on the computer readable storage media for execution by the processor via the computer readable memory.

19. The system of claim 17, further comprising:
fifth program instructions to determine that data describing the real-time physical conditions of the construct of the roadway fall outside a predetermined nominal range; and
sixth program instructions to initiate corrective measures to return a physical condition of the roadway back within the predetermined nominal range; and wherein
the fifth and sixth program instructions are stored on the computer readable storage media for execution by the processor via the computer readable memory.

20. The system of claim 17, further comprising:
fifth program instructions to determine that data describing the real-time physical conditions of the construct of the roadway fall outside a predetermined nominal range; and
sixth program instructions to initiate corrective measures to reroute traffic away from the roadway until the real-time physical conditions of the construct of the roadway return back within the predetermined nominal range; and wherein
the fifth and sixth program instructions are stored on the computer readable storage media for execution by the processor via the computer readable memory.

* * * * *